United States Patent

Su-yueh

[11] Patent Number: 6,160,480
[45] Date of Patent: Dec. 12, 2000

[54] WIRELESS INLINE-SKATE AND SKATE BOARD PULSE WATCH WITH SPEED AND HEART RATE MONITORING

[76] Inventor: Hsien Huang Su-yueh, No.68-1, Lane 496, Sec.1, Jong-Shan Road, Hwu-nēy Shiang, Gau-shyong Hsien, Taiwan

[21] Appl. No.: 09/404,827

[22] Filed: Sep. 24, 1999

[51] Int. Cl.[7] .................................................. G08B 23/00
[52] U.S. Cl. .................. 340/573.1; 340/669; 340/691.1; 340/691.6; 128/205 R
[58] Field of Search ................................. 340/573.1, 669, 340/570, 691.1, 691.4, 691.6; 600/500; 368/2; 128/205 R

[56] References Cited

U.S. PATENT DOCUMENTS

| | | | |
|---|---|---|---|
| 3,807,388 | 4/1974 | Ott et al. ............................. | 128/205 R |
| 5,511,045 | 4/1996 | Sasaki et al. ................................ | 368/2 |
| 5,670,944 | 9/1997 | Myllymaki .............................. | 340/573 |
| 5,807,267 | 9/1998 | Bryars et al. ............................ | 600/500 |
| 5,841,352 | 11/1998 | Prakash .................................... | 340/573 |

*Primary Examiner*—Jeffery A. Hofsass
*Assistant Examiner*—Phung Nguyen
*Attorney, Agent, or Firm*—Donald C. Casey, Esq.

[57] ABSTRACT

A wireless inline skate or skate board pulse watch which includes an inline skate or skate board transmitter worn on the user's foot to detect his body motion through a vibration switch and to moderate the detected signal into a radio signal is described. The watch further includes a heart rate pulse signal transmitter secured to the user's chest to detect his heart rate through a vibration switch and to modulate the detected signal into a radio signal. A timer is also provided, and a display unit which is worn on the user's wrist to receive and demodulate the output signals of the transmitters to show the data of speed/distance of the user's body motion and the number of beats per second of the user's heart through two separate display screens.

2 Claims, 7 Drawing Sheets

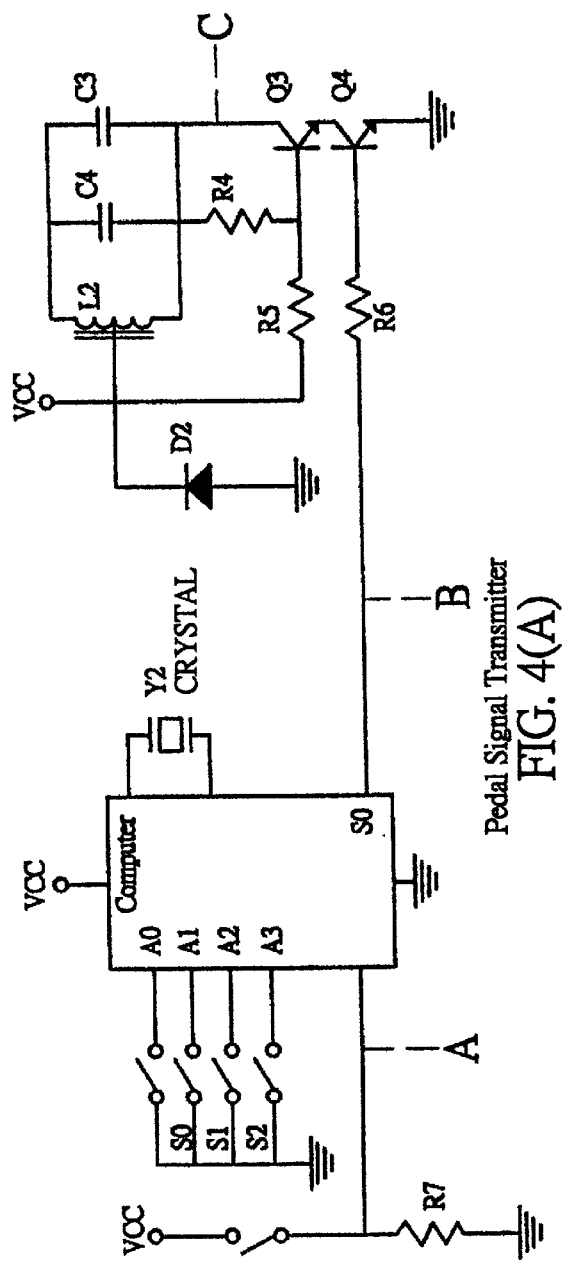
FIG. 4(A) Pedal Signal Transmitter
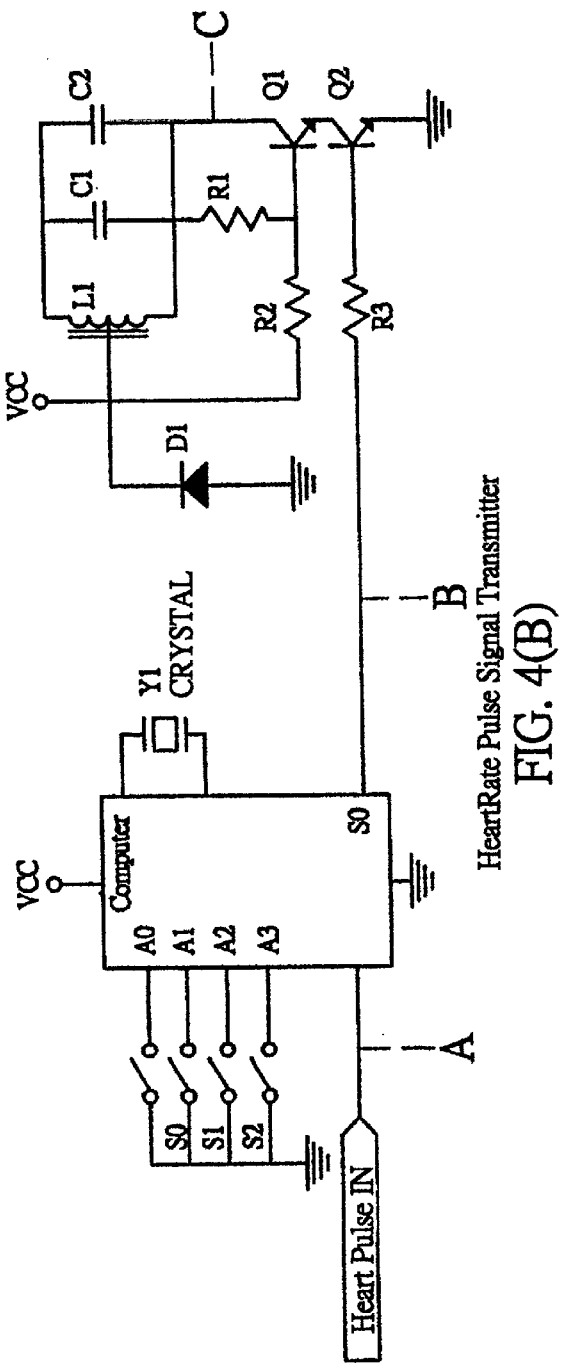
FIG. 4(B) HeartRate Pulse Signal Transmitter

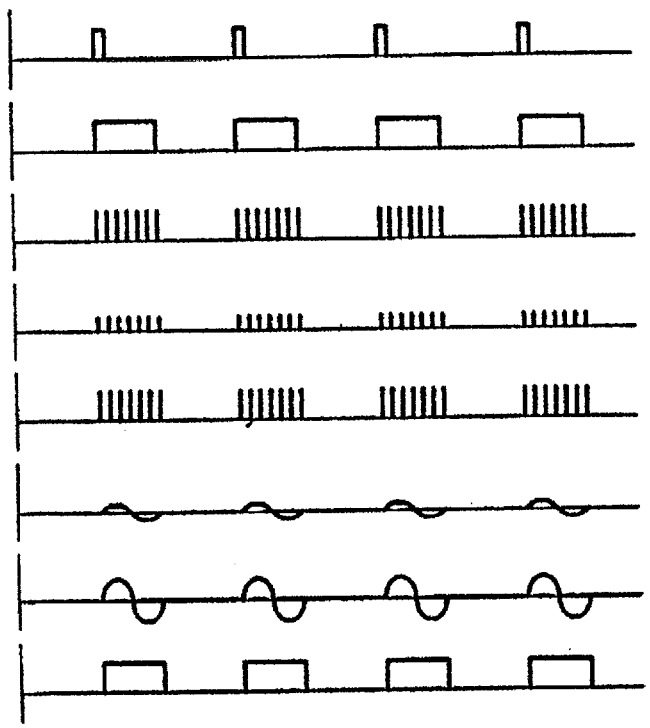
FIG. 6(A)
FIG. 6(B)
FIG. 6(C)
FIG. 6(D)
FIG. 6(E)
FIG. 6(F)
FIG. 6(G)
FIG. 6(H)
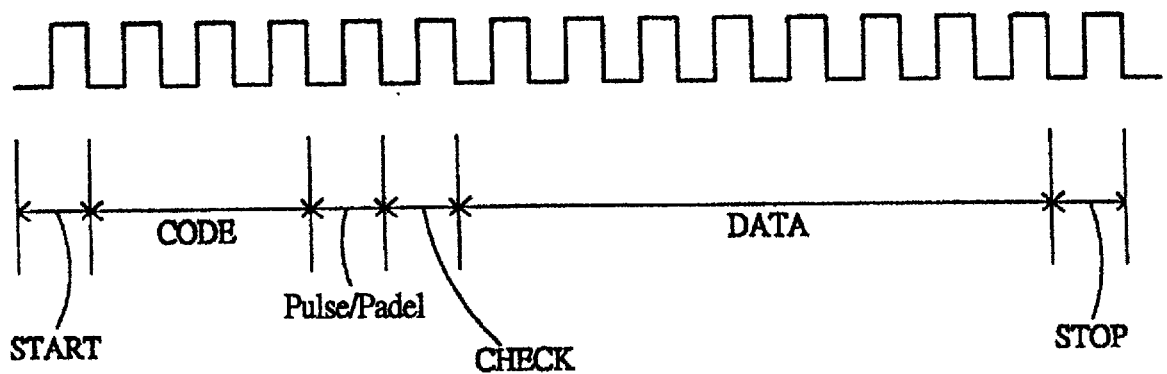
FIG. 7

WIRELESS INLINE-SKATE AND SKATE BOARD PULSE WATCH WITH SPEED AND HEART RATE MONITORING

BACKGROUND OF THE INVENTION

The present invention relates to a inline-pulse used for counting time speed/heart rate, and more particularly to a wireless inline pulse watch which enables the user to monitor one's exercising status without affect exercising performance.

FIGS. 1B, 1C, 1D and 1E show inline skate 1 that records the distance a walker covers by responding to measure the speed of inline-skate for users.

This structure and inline slate 1, as shown in FIG. 1A, comprises a vibration switch 11, a signal generator 12, which outputs a voltage signal corresponding to the switching frequency of the vibration switch 11, a debouncing circuit 13, which stabilizes the voltage signal from the signal generator 12, a quartz oscillator 14, which provides a clock signal, an operation processor 15, which counts the switching frequency of the vibration switch 11 and controls the operation of the quart oscillator 14, and a display 16 for displaying output data from the operation processor 15. Because the display unit of inline skate to be installed on the foot, the user cannot easily monitor the display during exercising.

SUMMARY OF THE INVENTION

The present invention has been accomplished to provide a wireless inline-skate board-pulse watch which eliminates the aforesaid problem. It is one object of the present invention to provide a wireless pulse watch which is capable of measuring time, speed and recording the distance of a walker and his heart rate. It is another object of the present invention to provide a wireless inline skate or skate board pulse watch which enables the user to monitor one's exercising status without causing an interference to one's exercising performance. To achieve these and other objects of the present invention, there is provided a wireless pulse watch comprised a inline signal transmitter worn on the foot to detect his running through a vibration switch and to modulate the detected signal into a radio signal, a heart rate pulse signal transmitter secured to the user's chest to detect his heart rate through a vibration switch and to modulate the detected signal into a radio signal, and a timer and display unit worn on the user's wrist to receive and demodulate the output signals of the transmitters, and to show the running speed and the data of the number of beats per second of the user's heat through two separate display screens.

BRIEF DESCRIPTION OF THE DRAWINGS

FIG. 4A is a circuit diagram of a inline signal transmitter for the wireless inline skate or skate board pulse watch according to the present invention.

FIG. 4B is a circuit diagram of a heart rate pulse signal transmitter for the wireless inline skate or skate board pulse watch.

FIG. 6A is a waveform chart of a voltage obtained from output end A of FIG. 2A.

FIG. 6B is a waveform chart of a voltage obtained from output end B of FIG. 2A.

FIG. 6C is a waveform chart of a voltage obtained from output end C of FIG. 2A.

FIG. 6D is a waveform chart of a voltage obtained from output end D of FIG. 3A.

FIG. 6E is a waveform chart of a voltage obtained from output end E of FIG. 3A.

FIG. 6F is a waveform chart of a voltage obtained from output end F of FIG. 3A.

FIG. 6G is a waveform chart of a voltage obtained from output end G of FIG. 3A.

FIG. 6H is a waveform chart of a voltage obtained from output end H of FIG. 3A.

FIG. 7 is a diagram of a communication code signal according to the present invention.

DETAILED DESCRIPTION OF THE PREFERRED EMBODIMENT

Figure 1A:
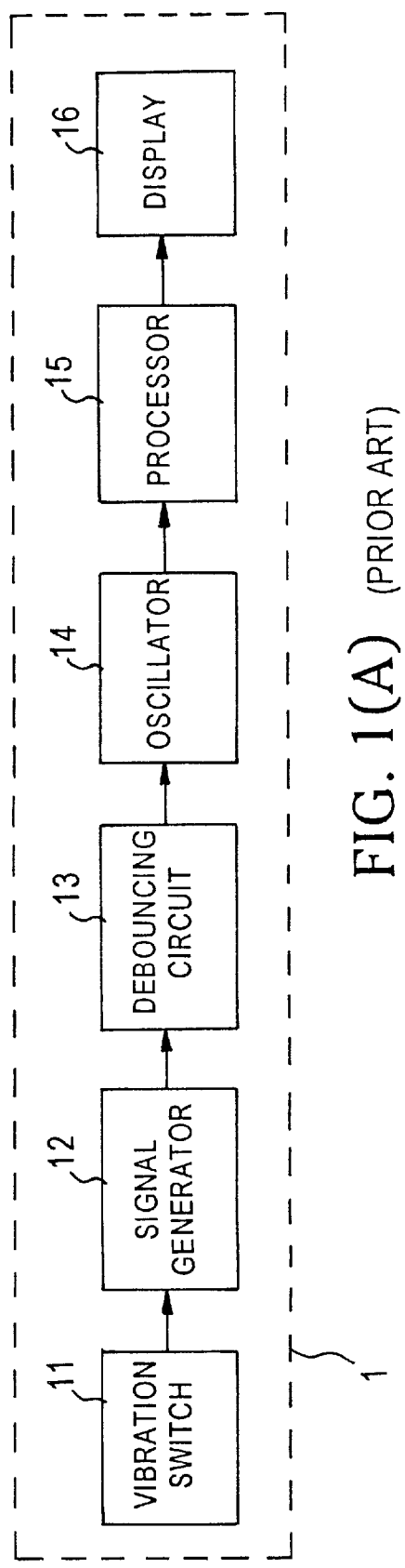
FIG. 1A is a circuit block diagram of a inline-skate board-pulse watch according to the prior art.
Figure 2A:
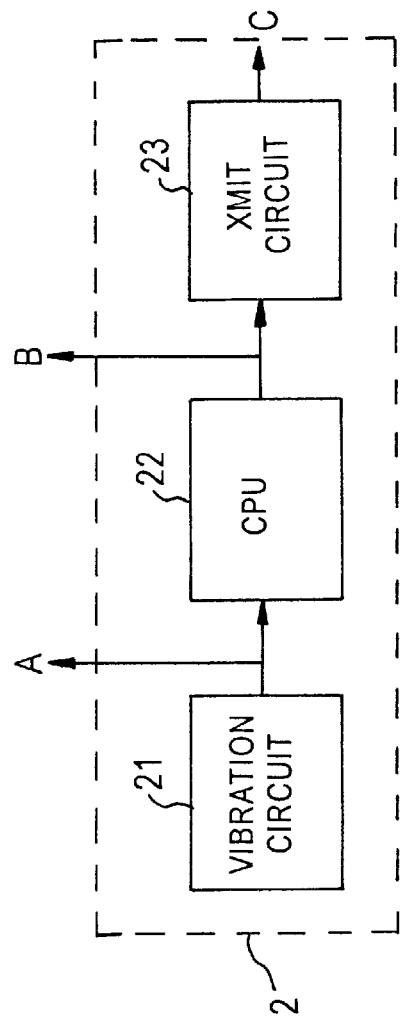
FIG. 2A is a circuit block diagram of a transmitter unit for a wireless inline skate or skate board pulse watch according to the present invention.
Figure 1C:
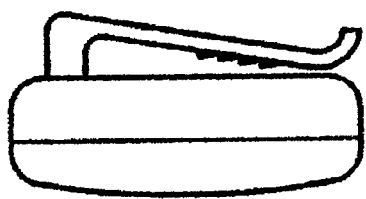
FIGS. 1B, 1C, 1D and 1E are three different views of the prior art inline-skate.
Figure 1E:
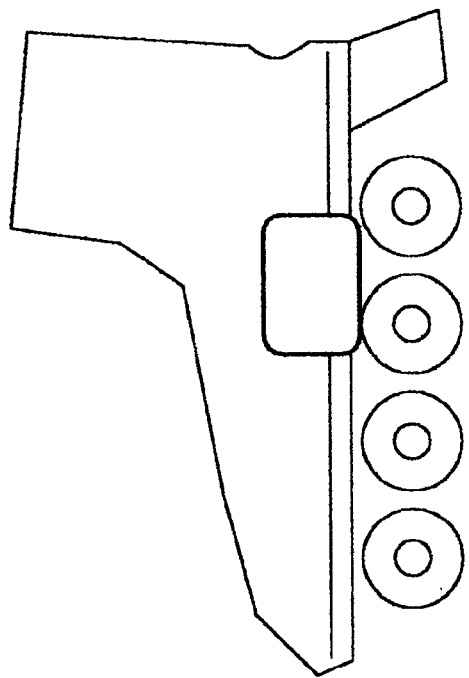
Figure 1B:
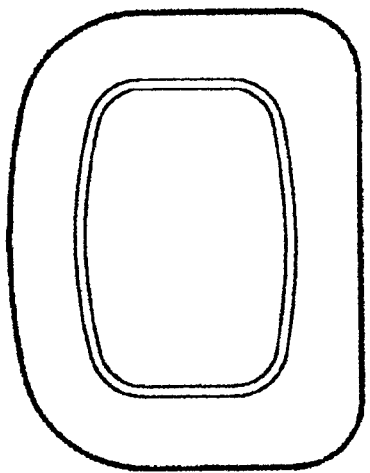
Figure 1D:
Figure 2B:
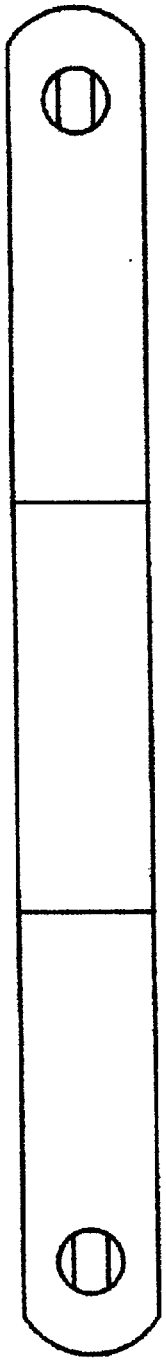
FIG. 2B is a front view of the transmitter unit according to the present invention.
Figure 2C:
FIG. 2C is a side view of the transmitter unit according to the present invention.

Referring to Figures from 2A through 3C, a wireless inline-skate board-pulse watch in accordance with the present invention comprises a transmitter unit 2 that can be fastened to the chest in front of the heart or installed on the inline skate or skate board, and a timer and display unit 3 that can be worn on the wrist.

Referring to Figures from 2A through 2C, 4A and 4B and 6A through 6C again, the transmitter unit 2 is comprised of a vibration switch 21, a CPU 22, and a modulation and transmitting circuit 23. The vibration switch 21 is attached to the chest in front of the heart or installed on the inline skate or skate board, and repeatedly triggered to output a signal corresponding to the speeding of the inline skate or skate board or the beating of the heart. The voltage waveform of the output signal from the vibration switch 21 (at output end A) is as shown in FIG. 6A. The output signal from the vibration switch 21 is sent to the CPU 22, and then synthesized through switches S0, S1, S2 into a communication code. The voltage waveform of the output signal (communication code signal) from the CPU 22 (at output end B)is a square wave as shown in FIG. 6B. The communication code signal from the CPU 22 is then modulated into a radio signal and transmitted to the timer and display unit 3 by the modulation and transmitting circuit 23. The waveform of the radio signal from the modulation and transmitting circuit 23 (at output end C) is as shown in FIG. 6C. Further, amplifier Q2 or Q4 is provided to amplify the output signal (heart rate pulse signal or inline signal) at output end B.

Referring to Figures from 3A through 3C, 6D through 6H and 7 again, the timer and display unit 3 comprises a receiving and demodulation circuit 31, a quartz vibrator 32, a CPU 33, a timer switch 34, and a display 35. The receiving and demodulation circuit 31 receives and demodulates every radio signal from the modulation and transmitting circuit 23 into a respective square wave voltage signal. The CPU 33 picks up every square wave voltage signal from the receiving and demodulation circuit 31, counts the number of signals received. The quartz oscillator 32 is controlled by the CPU 33 to count time. The timer switch 34 resets and starts the CPU 33 subject to a predetermined control procedure. The display 35 is comprised of a first display screen 351 for showing the number of inline signals, and a second display screen 352 for showing the number of heart rate pulse signals. The receiving and modulation circuit 31 is comprised of a frequency variable inductance-capacitance resonance circuit 311, which is induced to output a corresponding signal upon receipt of a radio signal from the transmitter unit 2, a three-stage amplifier circuit 312, which amplifies the output signal from the resonance circuit 311, and a waveform rectifying circuit 313, which rectifies the output signal from the three-stage amplifier circuit 312 into a square wave signal. The square wave signal outputted from the waveform rectifying circuit 313 is then sent to the CPU 33 for processing. The voltage wave form of the output signal from the resonance circuit 311 (at output end D) is shown in FIG. 6D. The three-stage amplifier circuit 312 comprises a first stage filter amplifier 3121, a second stage filter amplifier 3122, and a third stage filter amplifier 3123. The voltage waveform of the output signal from the stage filter amplifier 3121 (at output end E) is shown in FIG. 6E. The voltage waveform of the output signal from the second stage filter amplifier 3122 (at output end R) is shown in FIG. 6F. The voltage waveform of the output signal from the third stage filter amplifier 3123 (at output end G) is shown in FIG. 6G. The voltage waveform of the output signal from the waveform rectifying circuit 313 (at output end H) is shown in FIG. 6H.

Figure 3B:
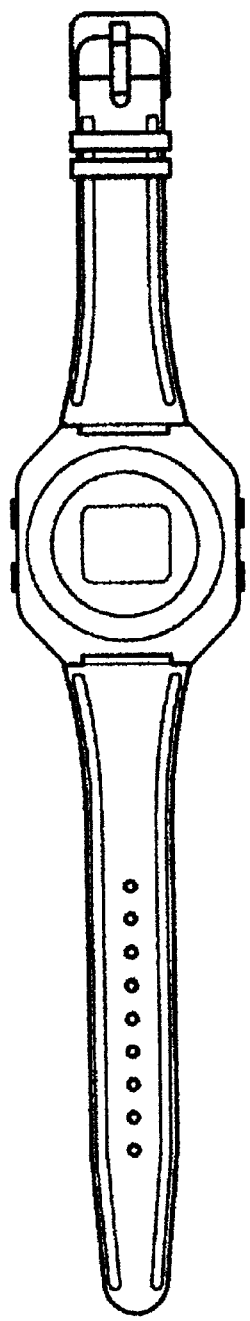
FIG. 3B is a front view of the timer and display unit according to the present invention.
Figure 3C:
FIG. 3C is a side view of the timer and display unit according to the present invention.
Figure 3A:
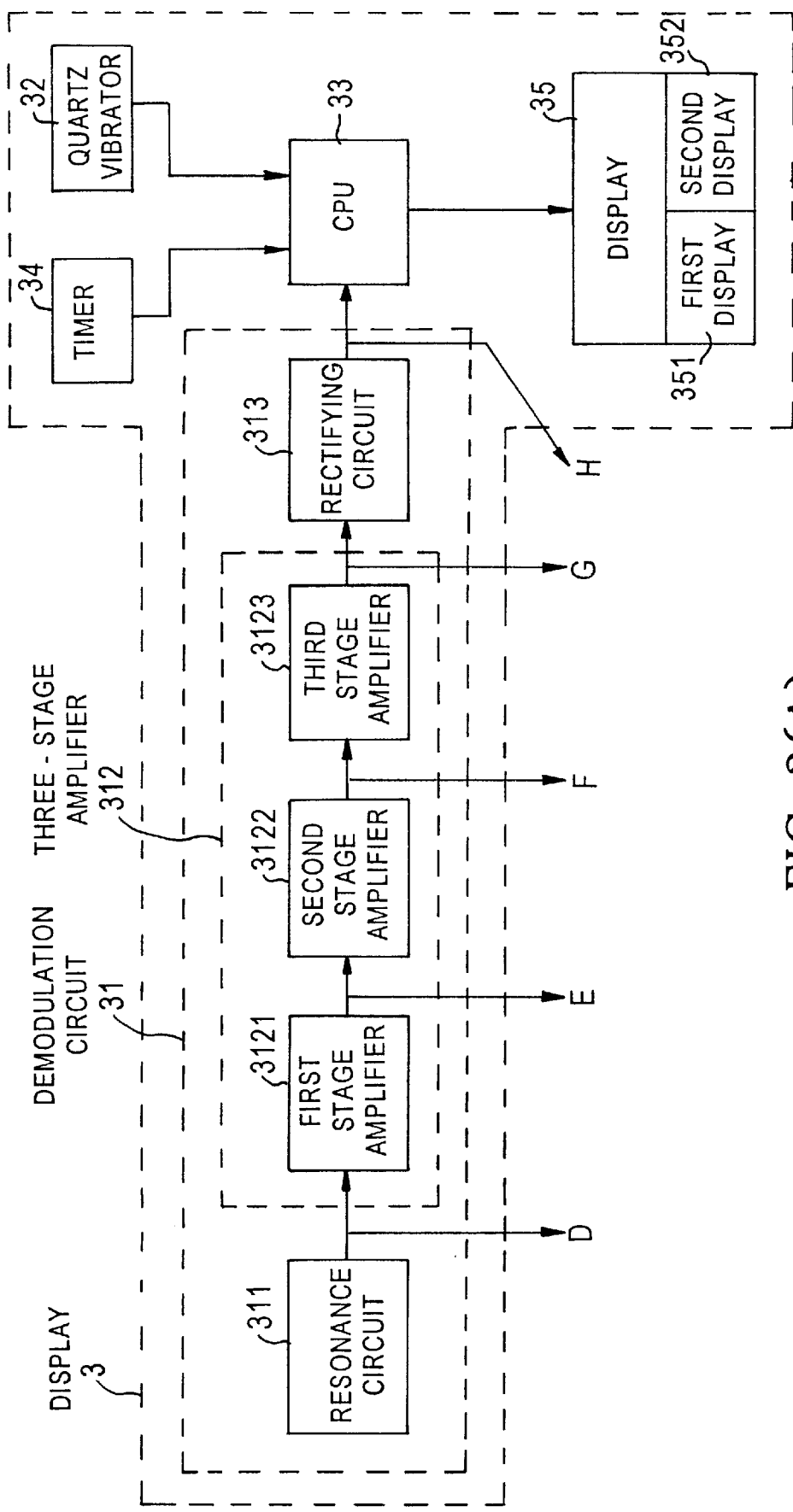
FIG. 3A is a circuit block diagram of a timer and display unit for the wireless inline skate or skate board pulse watch according to present invention.
Figure 5:
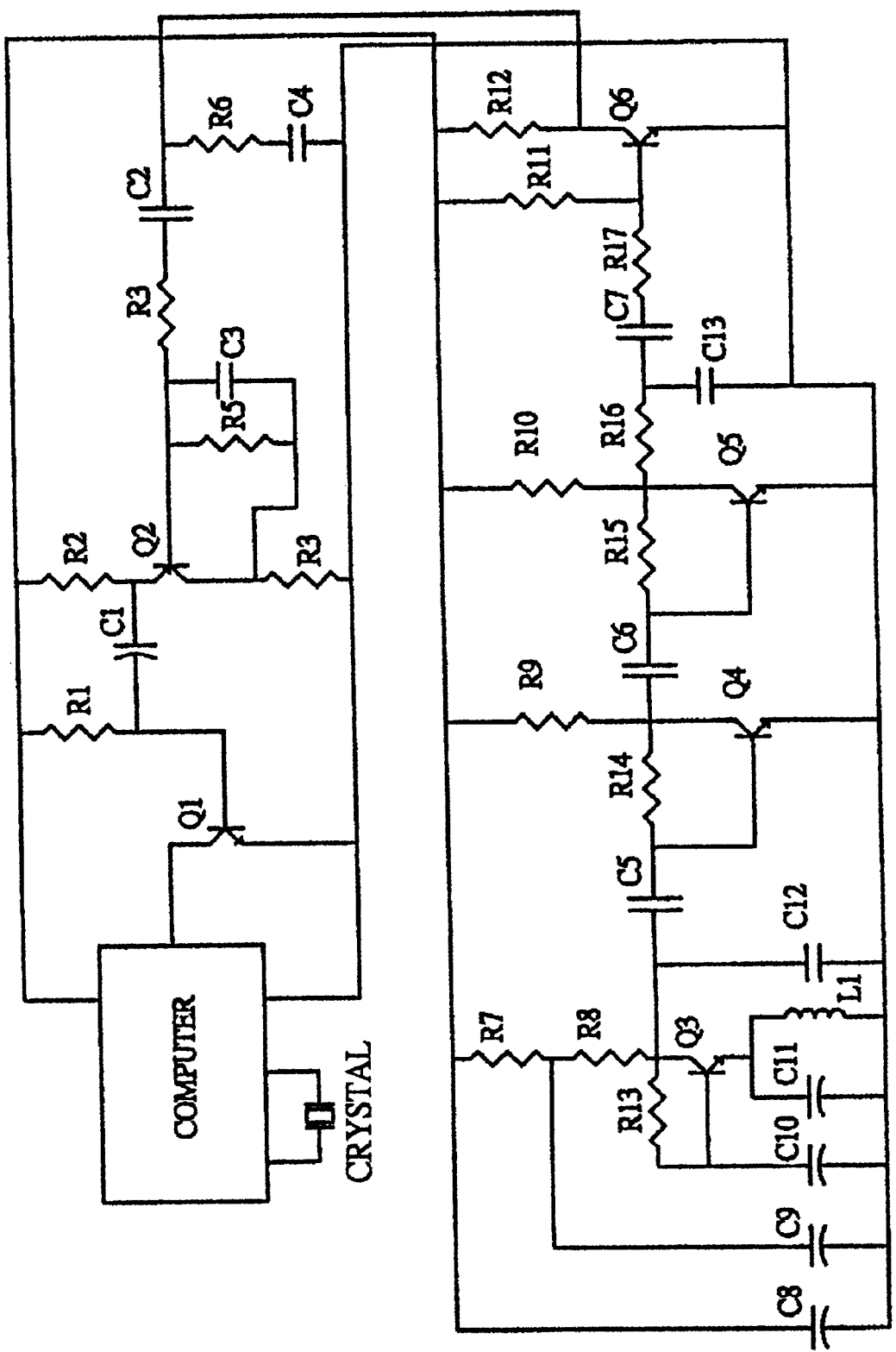
FIG. 5 is a circuit diagram of the timer and display unit according to the present invention.

The series communication code signal from the transmitter unit 2 is explained hereinafter with reference to FIG. 7. A communication code signal according to the present invention is a 15-bit signal, each bit of the 15-bit signal containing a high voltage referenced by 1, or a low voltage referenced by 0. The first bit is the start bit START. If the start bit is 1 (high potential), the receiving means (namely, the receiving and demodulation circuit of the aforesaid timer and display unit 3) is induced to receive the signal. The first three bits after the star bit form a code, and there are 8 selective combinations for the code. Therefore, when several inline-pulse watches are used, the output signals from the respective transmitter units will not interfere with each other. The fourth bit after the code is for function check. If the fourth bit of the 15-bit signal is 1 (high potential), the data of the signal is for inline counting. If the fourth bit of the 15-bit signal is 0 (low potential), the data of the signal is for heart rate pulse counting. The following 8 bits after the fourth bit form a data DATA. If the Transmitted data is for inline counting, it means that the user stands Still when DATA=00000000, or moves for one step when DATA=11111111. If the transmitted data is for heart rate pulse, the data represents the number of beats per minute of the heart. The last bit of the 15-bit communication ode signal is the top bit STOP, that informs the receiving means (the receiving and demodulation circuit of the aforesaid timer and display unit 3) to stop signal receiving. Through the communication code signal, the user's inline or skate board or heart rate condition is transmitted from the transmitter unit 2 to the timer and display unit 3. The timer and display unit 3 can be made in the form of a wrist watch (see FIGS. 3B and 3C) convenient for wearing on the wrist.

When in use, the transmitter unit 2 is secured to the chest in front of he heart or speeding on the inline skate or skate board, and the timer and display unit 3 is worn on the wrist. When exercising, the number the heart rate or speeding rate of the inline skate or skate board is counted and displayed through the display screen 351 or 352 of the display 35. The installation of the inline skate or skate board pulse watch does not interfere with the performance of exercising, and the user can monitor the exercising status as desired. Because the frequency of the resonance circuit 311 of the receiving and demodulation circuit 31 and the modulation and transmitting circuit 23 is changeable, signal interference can be eliminated when two inline-skate board-pulse watches are simultaneously used.

It is to be understood that the drawings are designed for Purposes of illustration only, and are not intended as a definition of the limits and scope of the invention disclosed.

What the invention claimed is:

1. A wireless inline skate or skate board pulse watch comprising:

a first transmitter installed on the inline skate, said first transmitter comprising a vibration switch moved with the inline skate or skate board to output a voltage signal corresponding to the user's foot motion, a CPU for processing data from the vibration switch of said first transmitter with encoder switches S0, S1, S2 thereof into a communication code signal, and a modulation and transmitting circuit which modulates the communication code signal, and a modulation and transmitting circuit which modulates the communication code signal from the CPU of said first transmitter into a radio inline skate or skate board signal and then transmits the radio signal thus obtained into the air;

a second transmitter secured to the user's chest in front of the heart to detect the user's heart rate, said second transmitter comprising a vibration switch vibrated with the beating of the user's heart to output a voltage signal corresponding to the user's heart rate, a CPU for processing data from the vibration switch of said second transmission with encoder switches S0, S1, S2 thereof into a communication code signal, and a modulation and transmitting circuit which modulates the communication code signal from the CPU of said second transmitter into a radio signal and then transmits the radio signal thus obtained into the air; and a timer and display unit worn on the user's wrist, said timer and display unit comprising a receiving and demodulation circuit, which receives the radio signals from said first transmitter and second transmitter unit and modulates the received signals into corresponding inline skate/skate board/hear rate pulse signals, a quartz vibrator, which provides a clock signal, a CPU, which counts the number of inline skate/skate board/heart rate pulse signals from said receiving and demodulation circuit and controls the operation of said quartz oscillator to count time, a timer switch, which is controlled to reset the CPU of said timer and display unit, and a display having a first display screen controlled by the CPU of said timer and display unit to display the data of the inline signal and a second display screen controlled by the CPU of said timer and display unit to display the data of heart rate pulse.

2. The wireless inline-pulse watch of claim 1 wherein said receiving and modulation circuit of said timer and display unit is comprised of a frequency variable inductance-capacitance resonance circuit, which is induced to output a corresponding signal upon receipt of a radio signal from said first transmitter unit or said second transmitter, an amplifier circuit, which amplifies the output signal from said resonance circuit, and a waveform rectifying circuit, which rectifies the output signal from said amplifier circuit into a square wave signal and outputs the square wave signal thus obtained to the CPU of said timer and display unit.

* * * * *